United States Patent [19]
Macoul

[11] Patent Number: 5,984,961
[45] Date of Patent: Nov. 16, 1999

[54] INTRACORNEAL PRISM AND METHOD OF IMPROVING VISION IN A HUMAN EYE HAVING MACULA DISEASE

[76] Inventor: Kenneth L. Macoul, 593 Prospect St., Methuen, Mass. 01844

[21] Appl. No.: 08/982,927

[22] Filed: Dec. 2, 1997

[51] Int. Cl.⁶ .................................................. A61F 2/14
[52] U.S. Cl. .................................................. 623/5
[58] Field of Search ............................... 623/4, 5; 606/5, 606/166; 351/175

[56] References Cited

U.S. PATENT DOCUMENTS

| | | | |
|---|---|---|---|
| 4,581,031 | 4/1986 | Koziol et al. | 351/175 |
| 4,596,578 | 6/1986 | Kelman | 623/6 |
| 4,648,400 | 3/1987 | Schneider et al. | 128/303.1 |
| 4,648,878 | 3/1987 | Kelman | 623/6 |
| 4,655,774 | 4/1987 | Choyce | 623/5 |
| 4,665,913 | 5/1987 | L'Esperance, Jr. | 128/303.1 |
| 4,666,446 | 5/1987 | Koziol et al. | 623/6 |
| 4,669,466 | 6/1987 | L'Esperance, Jr. | 128/303.1 |
| 4,753,526 | 6/1988 | Koester | 351/219 |
| 4,759,761 | 7/1988 | Portnoy | 623/6 |
| 4,787,903 | 11/1988 | Grendahl | 623/6 |
| 4,846,833 | 7/1989 | Cumming | 623/6 |
| 4,907,586 | 3/1990 | Bille et al. | 606/5 |
| 5,108,429 | 4/1992 | Wiley | 623/6 |
| 5,123,921 | 6/1992 | Werblin, et al. | 623/5 |
| 5,201,762 | 4/1993 | Hauber | 623/6 |
| 5,203,788 | 4/1993 | Wiley | 623/6 |
| 5,215,104 | 6/1993 | Steinert | 128/898 |
| 5,326,348 | 7/1994 | Nordan | 623/6 |
| 5,364,388 | 11/1994 | Koziol | 606/5 |
| 5,425,727 | 6/1995 | Koziol | 606/5 |
| 5,443,473 | 8/1995 | Miller et al. | 606/166 |
| 5,591,185 | 1/1997 | Kilmer et al. | 606/166 |
| 5,634,919 | 6/1997 | Azar | 606/5 |
| 5,683,457 | 11/1997 | Gupta et al. | 623/6 |
| 5,741,245 | 4/1998 | Cozean et al. | 606/5 |
| 5,782,911 | 7/1998 | Herrick | 623/5 |
| 5,846,457 | 12/1998 | Hoffman | 264/2.1 |
| 5,849,006 | 12/1998 | Frey et al. | 606/5 |

OTHER PUBLICATIONS

Girard, Louis J., B.S., M.D.,F.A.C.S., Corneal Surgery, Advanced techniques in ophthalmic microsurgery, vol. 2, 1981, pp. 32, 144, 145, 154, 155 and 168–171.

*Primary Examiner*—Gene Mancene
*Assistant Examiner*—Eduardo C. Robert
*Attorney, Agent, or Firm*—Pearson & Pearson

[57] ABSTRACT

A method for improving vision in a human eye having a macula disease and in particular macula degeneration by inducing a prism in the cornea of an eye using a laser beam to ablate the central cornea into a prismatic shape. Also, an apparatus and method for implanting a synthetic prism into the cornea is provided. The resulting prism either induced or implanted in the cornea directs rays of light away from a diseased area of the macula to an undiseased macula area of the retina for improved sight.

17 Claims, 5 Drawing Sheets

INTRACORNEAL PRISM AND METHOD OF IMPROVING VISION IN A HUMAN EYE HAVING MACULA DISEASE

BACKGROUND OF THE INVENTION

1. Field of the Invention

This invention relates to improving vision in a macula diseased eye and in particular to surgically inducing a prism or causing a prismatic affect in the cornea in order to displace light from the diseased macula area of the retina to an undiseased area of the retina, thereby improving eyesight.

2. Description of Related Art

Macula disease and, in particular, macula degeneration is a leading cause of blindness in adults. Macula disease involves the central area of the retina, and it is this area that is responsible for acute vision and receives most of the light focused by the cornea and lens of the eye. Macula disease very often leads to a loss of vision to a level of 20/200 or less. Since macula disease only involves the central area of the retina consisting of a few square millimeters in area, the peripheral vision is spared in the vast majority of patients. Over 95% of the retina is usually spared from macula degeneration. Since the macula is most important for acute vision such as driving, reading, etc., these patients are severely disabled despite the fact that they still maintain peripheral vision. Intraocular lenses which are implanted inside the eye in place of a surgically removed lens (usually during cataract surgery) have been designed with prisms incorporated in them in order to displace the focused light from the center of the diseased retina, i.e., the area of macula degeneration to a more healthy peripheral area of the macula. However, these lenses require opening the eye and removing the patient's own lens in order to achieve this result. Prisms can be placed in eyeglasses, but because the eye moves and the eyeglasses remain in a stationary position, this induces too much distortion and astigmatism and is not tolerated by patients.

U.S. Pat. No. 4,581,031, issued to Jeffrey E. Koziol et al., on Apr. 8, 1986, discloses an intraocular lens including a convex portion and a prismatic portion for use with patients having macula degeneration of the retina. In another U.S. Pat. No. 4,666,446, issued to Jeffrey E. Koziol et al., on May 19, 1987, an intraocular lens comprising converging and diverging optical portions are disclosed for patients having macula degeneration. The converging lens provides the patient with substantially the same vision experienced prior to implantation of the intraocular lens. The diverging lens when combined with converging lens located outside the eye provides a magnified retinal image of a given object with increased visual acuity but a restricted visual field. Thus, a patient is provided with the choice of unmagnified but peripherally unrestricted vision or magnified but peripherally restricted vision.

U.S. Pat. No. 4,759,761, issued to Vladimir Portnoy, on Jul. 26, 1988, discloses an intraocular lens with built-in mirrored surfaces which produce the effect of a folded telescope with a long focal distance. By greatly magnifying an object, a certain amount of useful vision is restored to a patient with macula degeneration.

U.S. Pat. No. 5,123,921, issued to Theodore P. Wenblin, on Jun. 23, 1992, discloses a lens for implantation into the cornea of the eye for providing correction for myopia and myopia with accompanying astigmatism wherein a corneal cap section is removed and an implant bed is created to receive the intracorneal lens.

U.S. Pat. No. 5,364,388, issued to Jeffrey E. Koziol on Nov. 15, 1994 discloses a radiant energy beam delivery system for corneal surgery wherein radiant energy beams may be focused in a linear configuration onto the external surface of the cornea or onto intrastromal areas of the cornea of an eye to ablate the cornea in a radial slot, circumferential curved slot, or lenticular pattern and thereby modify its curvature and refractive power. However, this patent relates to correcting nearsightedness and does not disclose inducing a prism into the cornea for overcoming macula degeneration by displacement of light waves away from a diseased macula area.

SUMMARY OF THE INVENTION

Accordingly, it is therefore an object of this invention to provide a method for treatment of macula disease and particularly macula degeneration in the human eye.

It is an object of this invention to provide a method for treatment of macula disease without surgically opening the eye.

It is another object of this invention to provide a method of inducing a prism means in the cornea of the eye in order to displace light rays from a diseased macula at the central area of the retina.

It is another object of the invention to implant a synthetic prism in the corneal stroma of the eye to displace light rays from a diseased macula area to a healthier paracentral macula area.

These objects are further accomplished by providing a method of improving vision in a human eye having macula disease and in particular macula degeneration comprising the step of providing a means for inducing a prism means in the anterior surface of a cornea of the eye for displacing light waves passing through the prism means from a diseased macula area to a more healthy macula area. The step of providing a means for inducing a prism comprises the step of using a laser to ablate the anterior surface of a cornea of the eye such as an excimer laser. The step of using a laser to ablate the anterior surface of the cornea comprises the step of using an erodible mask having a predetermined axis and depth for inducing the prism means; however, the use of such a mask is not required. The step of using a laser to ablate the anterior surface of a cornea includes the step of varying the axis and depth of ablation when inducing the prism means.

The objects are further accomplished by providing a method of improving vision in a human eye having macula disease and in particular macula degeneration comprising the steps of forming an opening in the cornea of the eye, providing a means for inducing a prism means within the stroma of the cornea for displacing light waves passing through the prism means from a diseased macula area to a more healthy area, and closing the anterior flap over the induced prism means. The step of forming the opening comprises the step of forming an anterior flap on the cornea. The step of forming the opening also comprises the steps of dissecting the cornea and forming a lamella pocket. The step of providing a means for inducing a prism means comprises the step of using a laser to ablate the stroma of a cornea of the eye such as an excimer laser. The step of using a laser to ablate the stroma of a cornea further comprises the step of using an erodible mask having a predetermined depth for inducing the prism; however, the use of such a mask is not required. The step of using a laser to ablate the stroma of a cornea includes the step of varying the axis and depth of ablation when inducing the prism means.

The objects are further accomplished by providing a method of improving vision in a human eye having macular disease and in particular macula degeneration comprising the steps of forming an opening in the cornea of the eye, implanting a prismatic means in the cornea for displacing light waves from a diseased macula area to a more healthy macula area, and closing the anterior flap over the implanted prismatic means. The step of forming the opening comprises the step of forming an anterior flap on the cornea. The step of forming the opening also comprises the steps of dissecting the cornea and forming a lamella pocket. The step of implanting a prismatic means includes the step of implanting a prism comprising high index of refraction material such as a silicone or polymethylmethacralate. The step of implanting a prismatic means comprises the step of varying the axis and power of the prismatic means to place an image in a healthy macula area.

The objects are further accomplished by providing an intrastromal implant for improving vision in a human eye having macular disease and in particular macula degeneration comprising prismatic means for displacing light waves, the prismatic means being implanted in a stromal area of a cornea of the eye for displacing the light waves from a diseased macula area to a more healthy macula area. The prismatic means is placed in the stromal area after a lamella corneal flap is formed and placed over the prismatic means. The implant comprises a synthetic prism. The synthetic prism comprises a high index of refraction material such as silicone or polymethylmethacralate.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF ILLUSTRATIVE EMBODIMENTS

Figure 1:
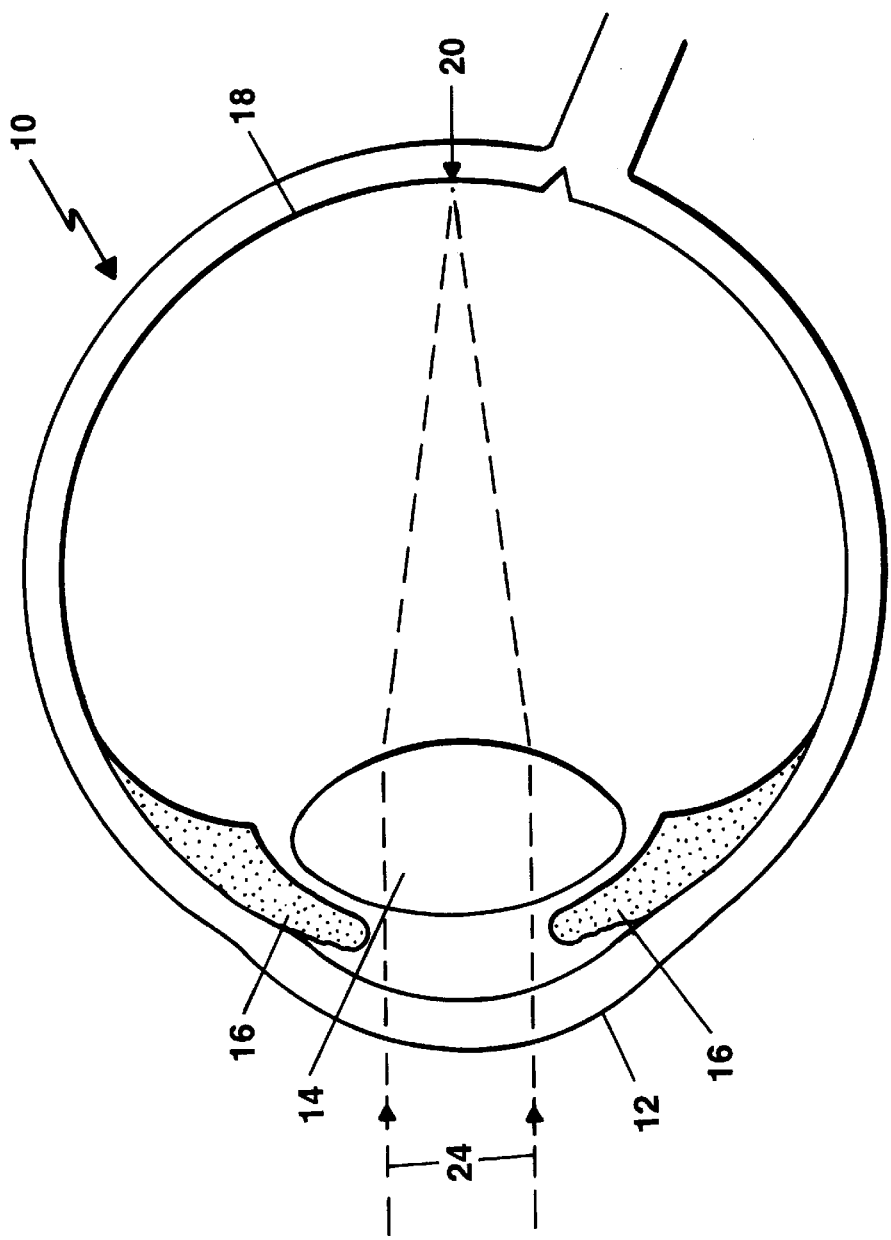
FIG. 1 is a side elevational view in longitudinal section of a schematic representation of a human eye.

Referring to FIG. 1, a human eye 10 is shown comprising the cornea 12, lens 14, iris 16, retina 18, and macula 20 located at the center of the retina. Incident light rays 24 enter the eye, pass through the cornea and are focused on the macula 20 by the lens 14. The macula 20 provides acute vision for distance as well as reading vision. Light rays which hit the cornea 12 and the lens 14 in a perpendicular fashion are focused directly on the macula 20. However, light rays which hit the cornea 12 and the lens 14 at a more oblique angle are focused on other parts of the retina and thus account for peripheral vision. When macula disease or in particular macula degeneration results, clear or acute vision for distance as well as reading vision are lost.

Figure 2:
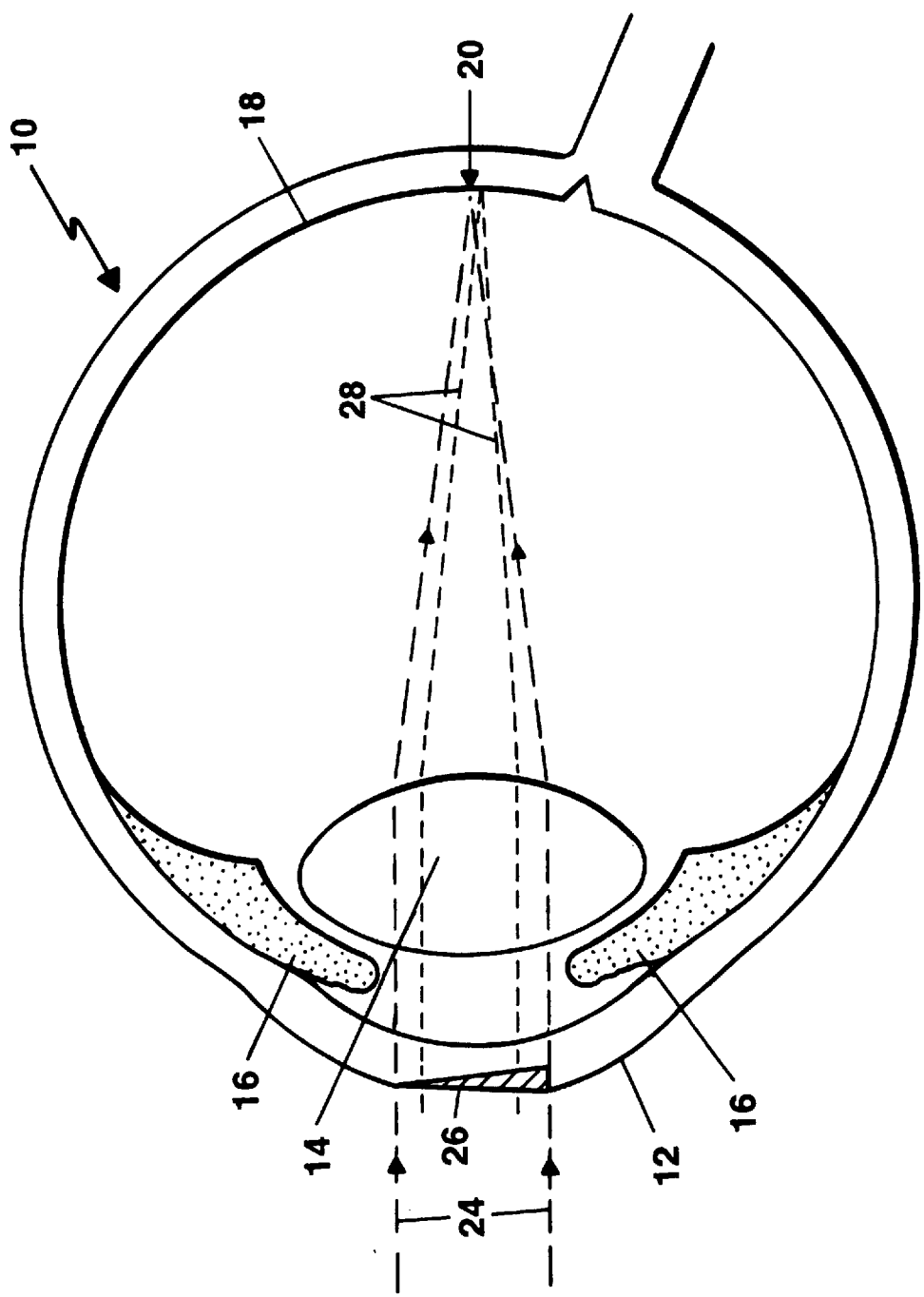
FIG. 2 is a side elevational view in longitudinal section of a human eye similar to that shown in FIG. 1 except that a prism is formed in the surface of the cornea by application of laser ablation, which causes a displacement of the light rays.

Referring now to FIG. 2, a side elevational view of the human eye 10 is shown which is similar to the eye 10 of FIG. 1 except that a prism 26 is formed in the surface of the cornea 12 by the application of laser ablation through the surface epithelium. The prism 26 causes light rays 24 to be displaced from the diseased central macula 20 to a healthy area of the macula as. As illustrated by displaced light rays 28. The prism 26 is formed by the use of an excimer laser such as Model APEX SVS manufactured by Summit Technology of Waltham, Mass. Other lasers may be approved by the U.S. Federal Drug Administration which may be used for ablation by ophthalmologists, such as scanning lasers.

Excimer lasers are well known in the art and have been used to ablate the cornea to correct nearsightedness, farsightedness, and astigmation. The parameters for inducing a prism are predetermined by animal studies as well as human studies. Parametric data is entered into a computer of the laser which automatically determines the depth, axis, etc. of the incident laser beam. The technical characteristics of the excimer laser beam hitting the eye are well known.

Ophthalmologists are trained in the use of the excimer lasers. Data regarding a particular eye is inserted into the computer and software performs required calculations and sets the laser beam characteristics for treatment. Keeping a patient still as the laser beam strikes the cornea is of course very important.

The laser ablation may also be performed using an erodible mask having a predetermined depth depending upon the thickness of the mask prior to application of the laser through the mask. The techniques of applying a laser beam with or without an erodible mask are well known in the ophthalmic industry and related literature.

Figure 3:
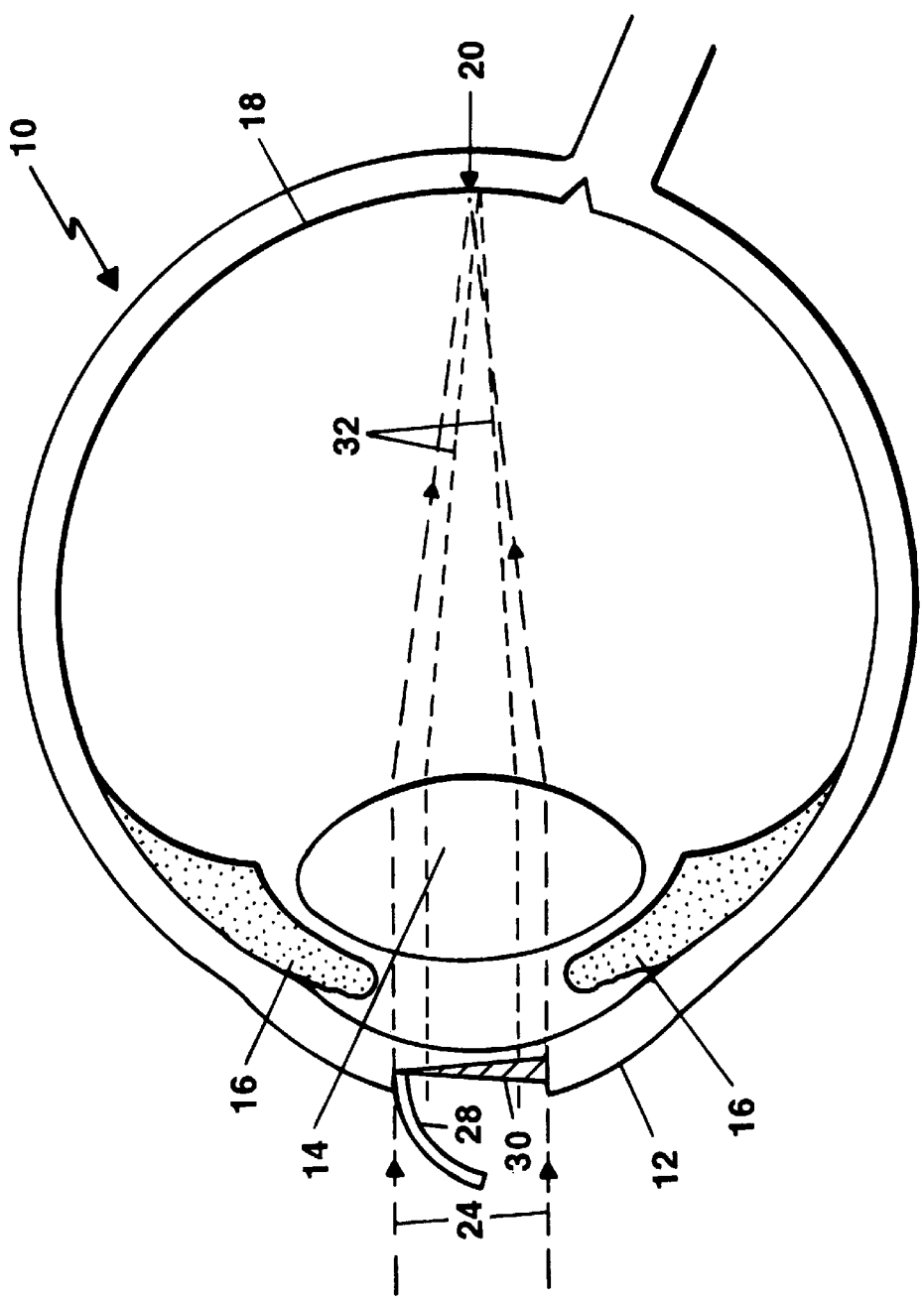
FIG. 3 is a side elevational view in longitudinal section of a human eye similar to that shown in FIG. 1 except that a hinged flap of the cornea is shown in front of a prism ablatively formed by application of a laser to the cornea, which causes a displacement of the light rays.

Referring now to FIG. 3, a side elevational view of the human eye 10 is shown similar to that shown in FIG. 1 except that a superficial flap 28 of the cornea 12 is prepared and then a prism 30 is formed in the stroma of the cornea 12. An excimer laser similar to that described above is used to accomplish the stroma ablation forming the prismatic shape. After the formation of the prism 30 the corneal flap 28 is replaced over the laser ablated area. When completed the light rays 24 are displaced away from the diseased area of the macula 20 to another less diseased area of the retina 18 such as the light rays 32 as shown in FIG. 3. The method of creating the prism as shown in FIG. 3 by preparing the superficial flap 28 is preferable over the method shown in FIG. 2 because the patient is more comfortable by doing the corneal flap and vision is usually restored faster than occurs with the superficial application of the laser.

Figure 4:
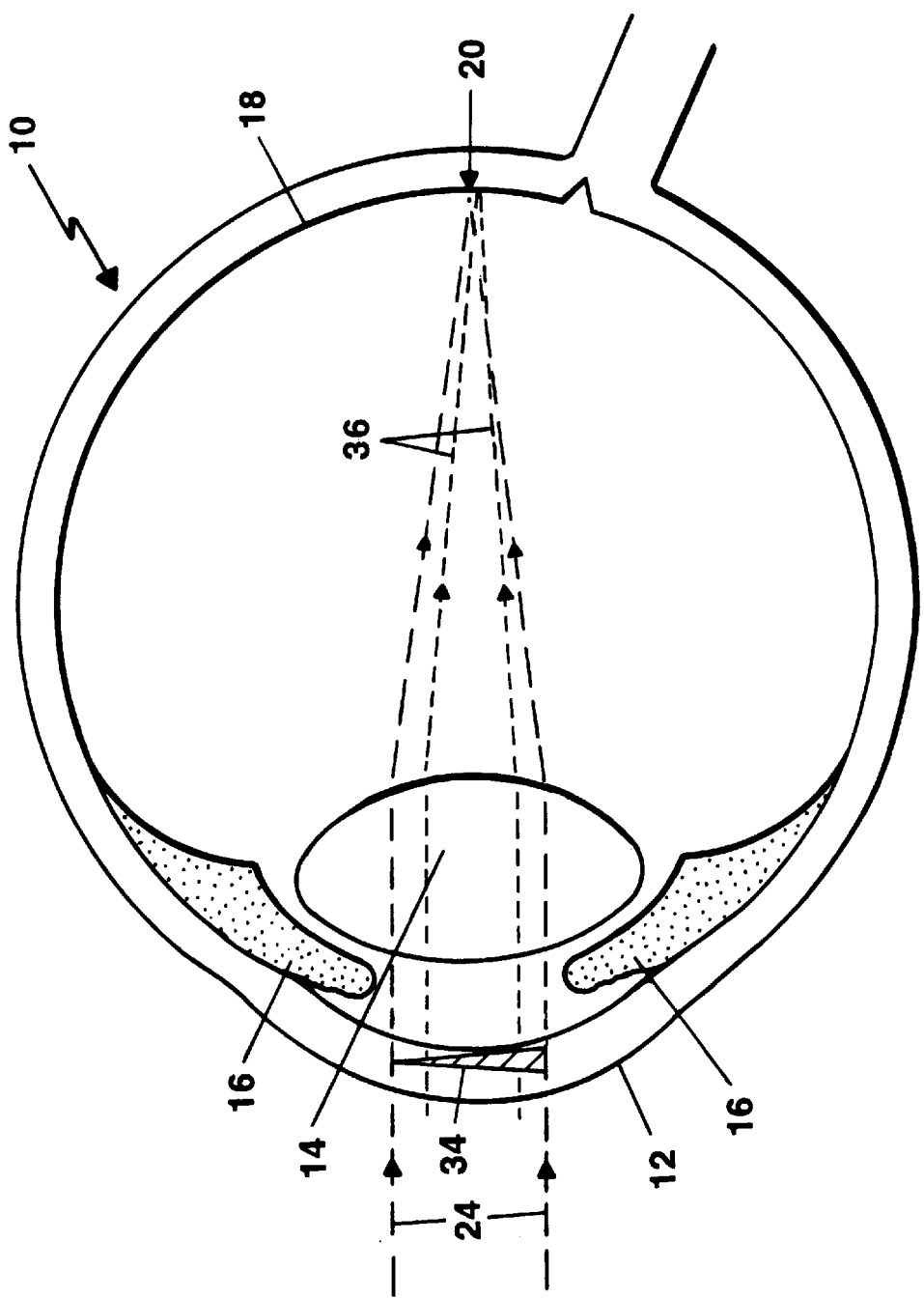
FIG. 4 is a side elevational view in longitudinal section of a human eye similar to that shown in FIG. 1 except that a synthetic prism is surgically inserted in the stroma of the cornea causing a displacement of the light rays.
Figure 7:
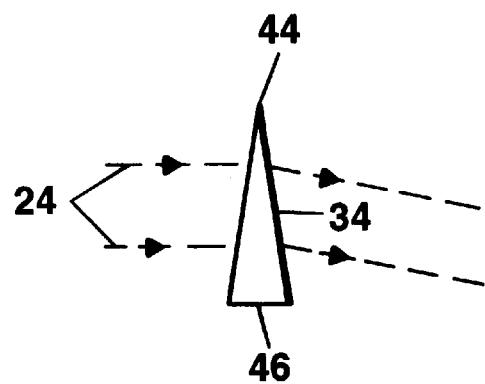
FIG. 7 shows a side elevational cross-sectional view of the synthetic prism which as shown in FIG. 4 is implanted in the stroma of the cornea and illustrates how the prism bends or displaces light waves downward toward its base.

Referring now to FIG. 4 and FIG. 7, a side elevational view of the human eye 10 is shown in FIG. 4 which is similar to that shown in FIG. 1, except that a synthetic prism 34 is surgically inserted into the stroma of the cornea 12. FIG. 7 shows a side elevational, cross-sectional view of the synthetic prism 34 illustrating the light waves 24 being bent or displaced downward toward its base after passing through the prism 34. Prior to insertion of the prism 34 a lamella corneal flap (not shown) is prepared and then replaced over the inserted prism 34. Such a "corneal flap" procedure is known in the prior art and used with a laser for nearsightedness, farsightedness and astigmation treatments. It is known as the LASIK procedure. The prism 34 may be thin enough so that a section of the cornea does not have to be removed. However, if a section has to be removed, it may be done surgically or with the laser. The light rays 24 entering the eye 10 become displaced light rays 36 focusing the light rays 36 away from the diseased area of the macula 20. The prism 34 is made from synthetic material such as silicone, polymethylmethacralate or another crystalline substance of high index of refraction as needed.

In the above embodiments shown in FIG. 2, FIG. 3 and FIG. 4, for the induction of a prismatic affect in the cornea 12, the axis of the prisms 26, 30 and 34 is determined preoperatively by determining the healthiest area of macula 20 and thus displacing light rays to the healthy area.

Figure 5:
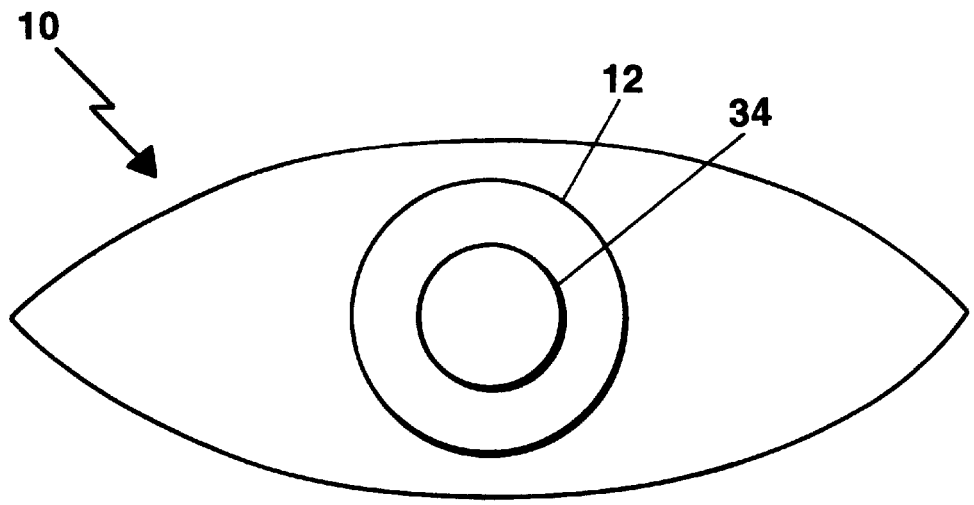
FIG. 5 is a front elevational outline view of a human eye showing that an intrastromal implant or laser ablation of the cornea is circular in shape.

Referring now to FIG. 5, a front elevational outline of a human eye is shown and within the eye a prism 34 formed by an intrastromal implant 34 or laser ablation 26, 30 of the cornea 12 is shown as being circular in shape. However, the prism 34 may be any shape such as square, etc.

Figure 6:
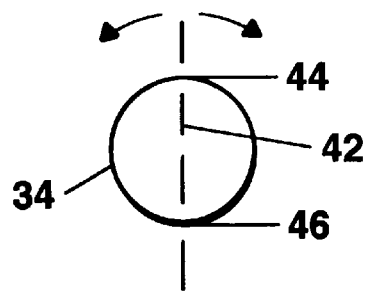
FIG. 6 shows a front elevational view of an intrastromal implant prism having an axis determined by the thinnest portion and the thickest portion, which can be rotated to the proper orientation in the cornea in order to displace the image from the macula.

Referring to FIG. 6, a front elevational view of an intrastromal implant prism 34 is shown having an axis determined by the thinnest portion 44 and the thickest portion 46 of the prism 34. The axis 42 of the prism 34 can be rotated to an appropriate position which is determined preoperatively to displace the image from a diseased macula to a more healthy area. The axis of rotation also applies to the laser ablation procedure since the induced prism by laser has an axis, and the healthiest area of the macula is determined preoperatively by testing. Positioning of the axis of the prism is determined by a number of tests that are available preoperatively and commonly known in the art, in order to determine the distance from the diseased area from which the image is displaced. Also, the axis of rotation applies to the laser ablation, since the induced prism by laser also has an axis and this is determined preoperatively by testing to find the healthiest area of the macula.

Various powers of synthetic prisms 34 can be made depending on the amount of displacement of the light rays that is desired. Also, the powers of the prism induced by the laser can be changed by varying the thickness of ablation by the laser and thus moving the light rays to the desired position. This invention has been disclosed in terms of certain embodiments. It will be apparent that many modifications can be made to the disclosed apparatus without departing from the invention. Therefore, it is the intent of the appended claims to cover all such variations and modifications as come within the true spirit and scope of this invention.

What is claimed as new and desired to be secured by Letters Patent of the United States is:

1. A method of improving vision in a human eye having macula disease including macula degeneration comprising the steps of:

forming an opening in a cornea of said eye;

providing a means for inducing a prism means in said opening within the stroma of said cornea for displacing light waves passing through said prism means from a diseased macula area to a more healthy area; and closing said opening over said induced prism.

2. The method as recited in claim 1 wherein the step of forming said opening comprises the step of forming an anterior flap on said cornea.

3. The method as recited in claim 1 wherein the step of forming said opening comprises the steps of dissecting said cornea and forming a lamella pocket.

4. The method as recited in claim 1 wherein said step of providing a means for inducing a prism means comprises the step of using a laser to ablate said stroma of a cornea of said eye.

5. The method as recited in claim 4 wherein said step of using a laser to ablate said stroma of a cornea of said eye comprises the step of using an excimer laser.

6. The method as recited in claim 4 wherein said step of using a laser to ablate said stroma of a cornea comprises the step of using an erodible mask having a predetermined depth for inducing said prism means.

7. The method as recited in claim 4 wherein said step of using a laser to ablate said stroma of a cornea includes the step of varying the axis and depth of ablation when inducing said prism means.

8. A method of improving vision in a human eye having macula disease including macula degeneration comprising the steps of:

forming an opening in a cornea of said eye;

implanting a prismatic means in said cornea for displacing light waves from a diseased macula area to a more healthy macula area by varying the axis and power of said prismatic means to place an image in said healthy macula area; and closing said opening over said implanted prismatic means.

9. The method as recited in claim 8 wherein the step of forming said opening comprises the step of forming an anterior flap on said cornea.

10. The method as recited in claim 8 wherein the step of forming said opening comprises the steps of dissecting said cornea and forming a lamella pocket.

11. The method as recited in claim 8 wherein said step of implanting a prismatic means includes the step of implanting a prism comprising a high index of refraction material including silicon.

12. The method as recited in claim 8 wherein said step of implanting a prismatic means includes the step of implanting a prism comprising a high index of refraction material including polymethylmethacralate.

13. An intrastromal implant for improving vision affected by macula disease including macula degeneration comprising:

means for opening a cornea;

prismatic means implanted in a stromal area of said cornea for displacing light waves from a diseased macula area to a more healthy macula area by varying the axis and power of said prismatic means to place an image in said healthy macula area; and means for closing said opening over said implanted prismatic means.

14. The intrastromal implant as recited in claim 13 wherein said prismatic means is placed in said stromal area after a lamella corneal flap is formed by said cornea opening means and said corneal flap is placed over said prismatic means.

15. The intrastromal implant as recited in claim 13 wherein said implant comprises a synthetic prism.

16. The intrastromal implant as recited in claim 15 wherein said synthetic prism comprises a high index of refraction material including silicone.

17. The intrastromal implant as recited in claim 15 wherein said synthetic prism comprises a high index of refraction material including polymethylmethacralate.

\* \* \* \* \*